United States Patent [19]

Dappen

[11] 4,283,491

[45] Aug. 11, 1981

[54] ANALYTICAL ELEMENTS WITH IMPROVED REAGENT STABILITY

[75] Inventor: Glen M. Dappen, Webster, N.Y.

[73] Assignee: Eastman Kodak Company, Rochester, N.Y.

[21] Appl. No.: 67,843

[22] Filed: Aug. 20, 1979

Related U.S. Application Data

[63] Continuation of Ser. No. 831,204, Sep. 6, 1977, abandoned.

[51] Int. Cl.³ .................... C12Q 1/62; C12Q 1/54; C12Q 1/28; C12N 9/96
[52] U.S. Cl. .................................. 435/10; 435/14; 435/25; 435/28; 435/188; 435/805; 435/810; 422/56; 422/61; 252/408
[58] Field of Search .............. 435/14, 28, 188, 192, 435/805, 810, 25, 10; 422/56, 61; 252/408 R

[56] References Cited

U.S. PATENT DOCUMENTS

| | | | |
|---|---|---|---|
| 2,923,734 | 2/1960 | Sheetz | 260/486 |
| 3,212,855 | 10/1965 | Mast et al. | 422/56 |
| 3,459,790 | 8/1969 | Smith | 260/483 |
| 3,506,707 | 4/1970 | Miller et al. | 260/513 |
| 3,598,704 | 8/1971 | Dahlquist et al. | 435/14 |
| 3,616,251 | 10/1971 | Linoli et al. | 435/12 |
| 3,630,957 | 12/1971 | Rey et al. | 252/408 |
| 3,929,482 | 12/1975 | Ponticello et al. | 96/114 |
| 3,939,130 | 2/1976 | Ponticello | 260/65 |
| 3,992,158 | 11/1976 | Przybylowicz et al. | 422/57 |
| 4,042,335 | 8/1977 | Clement | 422/56 |

OTHER PUBLICATIONS

"Analytical Elements with Improved Reagent Stability", *Research Disclosure*, No. 164, (Dec. 1977), No. 16472.

*Primary Examiner*—Thomas G. Wiseman
*Attorney, Agent, or Firm*—J. Jeffrey Hawley

[57] ABSTRACT

Elements for the analysis of aqueous liquids are described. Deterioration of test reagents, particularly peroxidase, during storage is reduced by inclusion in the elements of a co-polymer derived from hydrophobic, addition-polymerizable monomers.

30 Claims, 5 Drawing Figures

THE EFFECT OF THE ADDITION OF
THE LATEX ON THE FRESH RESPONSE
OF LEUCO DYE WEBS

LEUCO DYE, NO LATEX INTERMEDIATE
ENZYME STABILITY AFTER 4 WEEKS
AT 78° 50%

LEUCO DYE PLUS LATEX INTERMEDIATE
ENZYME STABILITY AFTER 4 WEEKS
AT 78° 50%

LEUCO DYE, NO LATEX INTERMEDIATE
ENZYME STABILITY AFTER 8 WEEKS
AT 42°F 50%RH

LEUCO DYE PLUS LATEX INTERMEDIATE
ENZYME STABILITY AFTER 8 WEEKS
AT 42°F 50% RH

ANALYTICAL ELEMENTS WITH IMPROVED REAGENT STABILITY

This is a continuation of application Ser. No. 831,204, filed Sept. 6, 1977 abandoned.

BACKGROUND OF THE INVENTION

1. Field of the Invention

The invention involves elements for the quantitative or semi-quantiative analysis of aqueous liquids. It particularly concerns analytical elements which contain peroxidase as one of the test reagents.

2. Description of the Related Art

It is well known to perform a quantitative or semi-quantitative analysis of an aqueous liquid by contacting that liquid with an analytical element containing a combination of reagents capable of yielding a detectable product in proportion to the concentration of a predetermined analyte in the aqueous liquid. As used herein "reagent" is intended to mean a material that is interactive with the predetermined analyte, a precursor of that analyte, or any material produced during the analysis of that analyte. Such interaction refers to chemical reactivity, catalytic activity, or any other form of chemical or physical interaction that can result in the ultimate production of a change in the element that is detectable by suitable measurement of radiant energy, usually in the visible light range of the spectrum.

One general group of particularly useful analytical elements utilizes an enzymatic assay wherein the predetermined analyte, upon contact with the analytical element, reacts with oxygen in the presence of a suitable enzyme contained in the element to produce a peroxide in proportion to the concentration of the predetermined analyte in the aqueous liquid being analyzed. A detectable product is then yielded by the reaction of this peroxide with an indicator composition in the presence of peroxidase, both of which are also contained in the analytical element. The detectable product is formed within the element in direct proportion to the peroxide present and thus, also in proportion to the concentration of the predetermined analyte in the aqueous liquid. Elements and analyses of this type are described for example in U.S. Pat. No. 3,992,158 and in a copending U.S. application by Barbara J. Bruschi, Ser. No. 712,972, filed Aug. 9, 1976, U.S. Pat. No. 4,089,747, both of which are incorporated herein by reference. Such elements usually contain the test reagents described above, including peroxidase, in a carrier material that is permeable to aqueous liquids and to the predetermined analyte of choice. The term "predetermined analyte" is meant to refer to the substance whose concentration is intended to be measured during the analysis. The carrier may be the main material forming the element or just one layer in a multi-layered element. Its permeability assures that the aqueous liquid and predetermined analyte will come into contact with each of the test reagents contained in the carrier when such aqueous liquid is brought into contact with the carrier.

One of the advantages of such analytical elements is that analyses can be performed quickly and reliably by persons with little technical training and no access to a "wet" chemical laboratory. A doctor, for instance, might find it extremely useful to store a supply of various elements of this type for use in "on-the-spot" analyses of body fluids such as urine or blood serum as an aid to diagnoses.

Unfortunately, because of the carrier's necessary permeability to aqueous liquids, the test reagents contained in the carrier may deteriorate during significant periods of storage and thus deleteriously affect the accuracy and reliability of the analysis. For example, exposure to air and moisture may adversely affect the ability of peroxidase contained in a test element to catalyze the oxidation of an indicator composition by a peroxide, thus preventing the formation of detectable product accurately and consistently in proportion to the concentration of predetermined analyte.

In order to improve the stability of reactants during periods of storage it has been thought desirable to construct the carrier totally from a hydrophobic material to block moisture and air from penetrating to the test reagents, such as in U.S. Pat. No. 3,630,957. Unfortunately, such carriers are not sufficiently permeable to aqueous liquids and therefore would not be useful for analyses which require that aqueous liquids be able to penetrate to the test reagents.

U.S. Pat. Nos. 3,212,855 and 3,598,704, suggest adding water-soluble polymers or hydrophilic colloids to a bibulous carrier to keep test reagents physically separated and to help prevent deterioration of such reagents because of the effects of moisture. Although such polymers may slow the rate of penetration of moisture and air to test reagents, since they are water soluble polymers, it is clear that moisture will eventually penetrate them. The protection they afford is therefore limited.

U.S. Pat. No. 3,616,251, suggests imbedding the test reagents into the surface of a carrier material comprising a hydrophobic polymer by using an organic solvent, but the stated purpose is to prevent the reagents from washing away when contacted with aqueous liquids, and it appears that the reagents would still be susceptible to the deteriorative chemical effects of moisture and air.

A different problem may additionally occur when an analytical element comprises a carrier permeable to aqueous liquids which is coated on a hydrophobic support material. It involves unwanted curl. This is caused by absorption and evaporation of moisture in the carrier resulting in swelling and shrinking of the carrier relative to the support material, which does not absorb or evaporate moisture. This problem is well known in the photographic industry, where materials such as gelatin are coated on hydrophobic support materials to form photographic films. U.S. Pat. No. 3,459,790, suggests the inclusion of certain hydrophobic polymers in gelatin layers of photographic films to alleviate this problem.

In light of the discussion above it would be desirable if an analytical element could be devised which comprises a carrier that is permeable to aqueous liquids and contains test reagents such as peroxidase, but the analytical element does not suffer from the above-mentioned problem of instability of reactants such as peroxidase during periods of storage. The present invention provides such an element.

SUMMARY OF THE INVENTION

It has been unexpectedly found that certain polymers, when dispersed in carrier materials permeable to aqueous liquids, can provide the desirable effect of improved stability of reagents such as peroxidase. It is particularly surprising that the stability of peroxidase is improved, because, although the polymers of choice are copolymers derived in large part from hydrophobic, addition-polymerizable monomers, they are merely dispersed within a carrier material permeable to aqueous liquids, and this carrier remains very permeable to aqueous liquids and to oxygen. One would expect that, since moisture and oxygen can still penetrate the carrier and come into contact with the reagents, reagents such as peroxidase, which could deteriorate during periods of storage in the prior art elements, would also deteriorate in the present elements. However, this is not the case. Although the reason for this result is not understood at this time, inclusion of the polymers described hereinafter in fact significantly improves reagent stability even though the ability of the carrier to be permeated by moisture and oxygen is not affected.

Accordingly, the invention provides an improved element for the analysis of a predetermined analyte in an aqueous liquid. The element comprises a carrier that is permeable to the predetermined analyte and to aqueous liquids. Alternatively, the carrier may be one layer of a multi-layered element. Dispersed in the carrier are reagents (one of which is peroxidase) which are capable of interacting with or facilitating interaction with the predetermined analyte or its reaction products to yield a detectable product. Also dispersed in the carrier is a polymer which is a copolymer comprising: from about 80 to about 98 percent by weight of recurring units derived from one or more hydrophobic addition-polymerizable monomers; from about 1 to about 20 percent by weight of recurring units derived from one or more anionic monomers; and from 0 to about 15 percent by weight of recurring units derived from one or more crosslinkable, active methylene group-containing monomers. Preferred polymers comprise: from about 80 to about 98 percent by weight of recurring units derived from one or more hydrophobic, addition-polymerizable monomers selected from the group consisting of an alkyl acrylate, an alkyl methacrylate, styrene, and a substituted styrene; from about 1 to about 20 percent by weight of recurring units derived from one or more anionic monomers selected from the group consisting of an acrylic acid, an acrylic acid salt, a methacrylic acid, a methacrylic acid salt, a sulfonic acid, a sulfonic acid salt, a sulfonate, a sulfate, a phosphate, and a phosphorate; and from 0 to about 15 percent by weight of recurring units derived from one or more crosslinkable, active methylene group-containing monomers.

The polymer should normally comprise from about 20 to about 50 percent of the total weight of the carrier plus the hydrophobic polymer.

DESCRIPTION OF THE PREFERRED EMBODIMENTS

Figure 1:
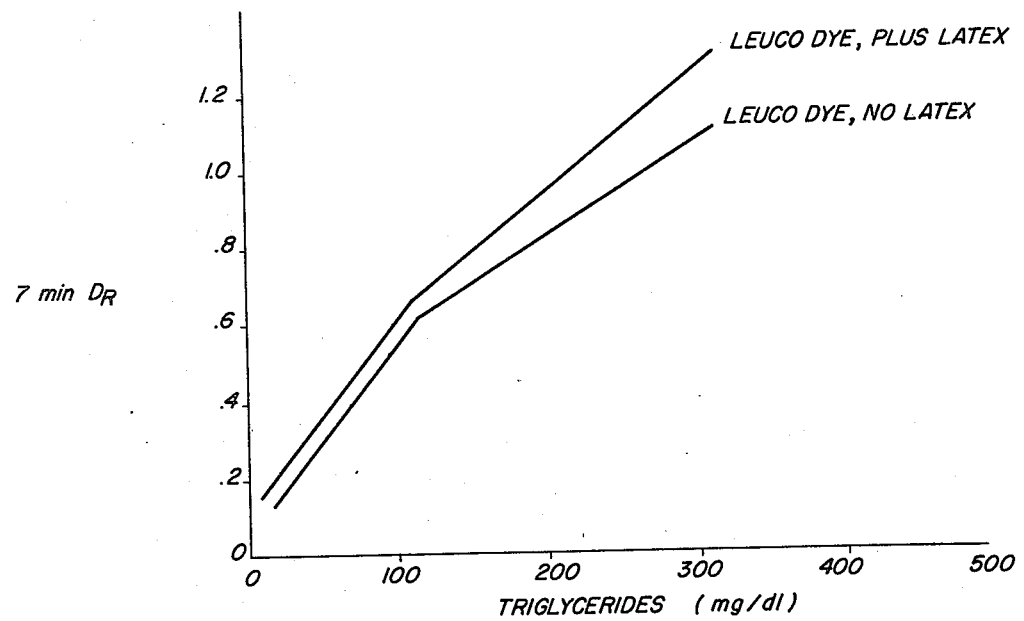
Figure 2A:
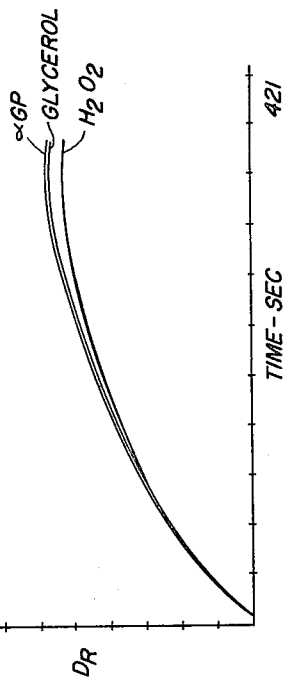
Figure 2B:
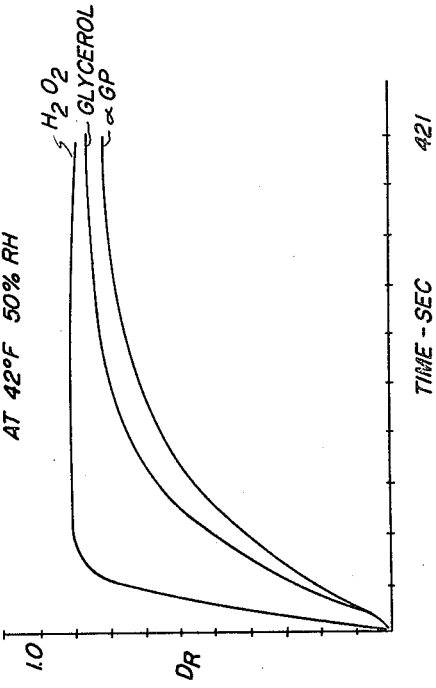
Figure 2C:
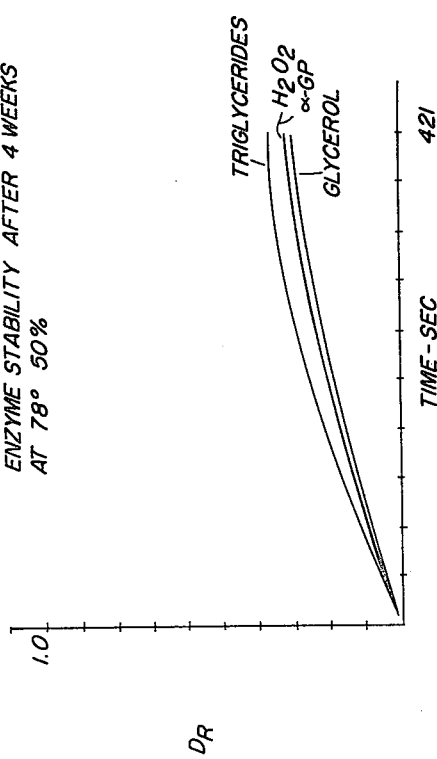
Figure 2D:
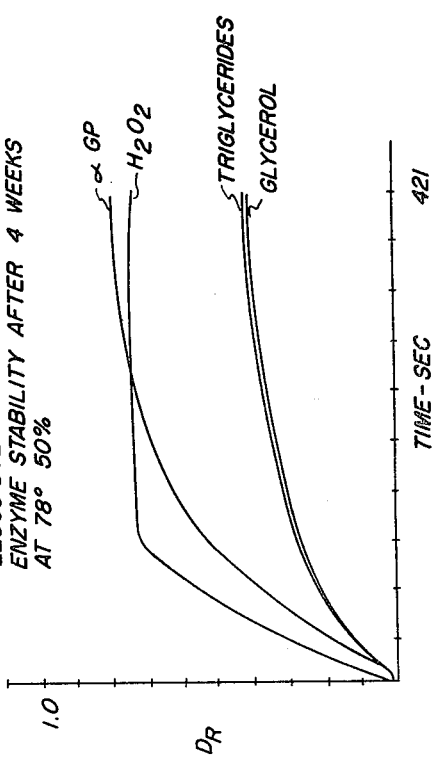

The invention achieves an improvement over the analytical elements of the prior art by dispersing polymers of the types described in the Summary of the Invention in a carrier that is permeable to aqueous liquids and predetermined analyte. The useful polymers as already described comprise: from about 80 to about 98 percent by weight of recurring units derived from one or more hydrophobic addition-polymerizable monomers, from about 1 to about 20 percent by weight of recurring units derived from one or more anionic monomers, and from 0 to about 15 percent by weight of recurring units derived from one or more crosslinkable, active methylene group-containing monomers.

Preferred classes of these polymers comprise: from about 80 to about 98 percent by weight of recurring units derived from one or more hydrophobic, addition-polymerizable monomers such as alkyl acrylates, alkyl methacrylates, styrene, and substituted styrenes; from about 1 to about 20 percent by weight of recurring units derived from one or more anionic monomers such as acrylic acid, methacrylic acid, sulfonic acids, sulfonates, sulfates, phosphates, and phosphorates, including the salts of the aforementioned acids, preferably the ammonium or alkali metal salts thereof, preferred monomers being sulfoalkyl acrylates, sulfoalkyl methacrylates, sulfoalkylacrylamides, and sulfoalkylmethacrylamides, for example, as described in U.S. Pat. Nos. 2,923,734 and 3,506,707; and 0–15, preferably 2 to 10, weight percent of recurring units derived from one or more crosslinkable, active methylene group-containing monomers such as described in U.S. Pat. Nos. 3,459,790, 3,929,482, and 3,939,130, a preferred monomer being 2-acetoacetoxyethyl methacrylate.

These preferred classes include, among others, the following specific polymers which have been found particularly useful in the analytical elements of this invention:

Poly(methyl acrylate-co-3-acryloyloxypropane=sulfonic acid, sodium salt-co-2-acetoacetoxyethyl methacrylate) (weight ratio 88.75:4.75:6.5);

Poly(methyl acrylate-co-2-acrylamido-2-methyl=propanesulfonic acid-co-2-acetoacetoxyethyl methacrylate) (weight ratio 88.75:4.75:6.5);

Poly(methyl acrylate-co-2-acrylamido-2-methyl=propanesulfonic acid-co-2-acetoacetoxyethyl methacrylate) (weight ratio=85:10:5);

Poly(n-butyl acrylate-co-3-acryloyloxypropane=sulfonic acid, sodium salt-co-2-acetoacetoxyethyl methacrylate) (weight ratio 91:25:4.75:4.0); and Poly(n-butyl acrylate-co-2-acrylamido-2-methylpropane sulfonic acid-co-2-acetoacetoxyethyl methacrylate) (weight ratio 85:10:5).

The methods of making such polymers are well known to those skilled in the art and the monomers are either readily available or their methods of synthesis are well known.

As previously stated, the useful polymers described above are dispersed in a carrier which may itself form the bulk of the analytical element, or alternatively, the carrier may be only one layer of a multi-layered element. In either case the carrier comprises a material permeable to aqueous liquids and to the predetermined analyte. The choice of a material is, of course, variable and dependent on the intended use of the element and may comprise naturally occurring hydrophilic substances like gelatin, gelatin derivatives, hydrophilic cellulose derivatives, polysaccharides such as dextran, gum arabic, agarose and the like, and also synthetic hydrophilic substances such as water-soluble polyvinyl compounds like poly(vinyl alcohol) and poly(vinyl pyrrolidone), water-soluble acrylamide polymers, etc. The choice may also depend partly on optical properties of the resultant carrier if photometric sensing of the analytical result is intended.

If the carrier is one layer of a multi-layered element, there may also be other layers such as spreading, reflecting, blocking, subbing, support, filtration, or registration layers as described in U.S. Pat. Nos. 3,992,158 and 4,042,335 incorporated herein by reference. These patents also describe methods widely used to fabricate such multi-layered elements. Particularly useful layers are a support layer comprising a hydrophobic material like polyethylene terephthalate onto which the carrier is coated and a spreading-reflecting layer coated over the carrier and comprising a blushed polymer and a pigment, for example, cellulose acetate and titanium dioxide. Furthermore, the element may incorporate multiple carrier layers.

In addition to the copolymer of choice, the carrier has distributed within it one or more reagents necessary to interact with or facilitate interaction with the predetermined analyte or its reaction products to yield a detectable product. In analytical elements of this invention peroxidase is one of these reagents. The choice of others depends on the analysis to be performed. For example, other reagents might include a suitable enzyme to catalyze the oxidation of the predetermined analyte to yield a peroxide, an indicator composition capable of reacting with peroxide in the presence of peroxidase to yield a detectable product, a compound for controlling pH, etc. A number of useful indicator compositions are described in copending U.S. application Ser. No. 712,972, U.S. Pat. No. 4,089,747, filed Aug. 9, 1976, by Barbara J. Bruschi, incorporated herein by reference. Such specific examples include an element for the analysis of glucose which might contain such reagents as glucose oxidase, peroxidase, 7-hydroxy-1-naphthol, 4-amino-antipyrene HCl, and a phosphate buffer system at pH 6; and an element for the analysis of uric acid which might contain such reagents as bis(vinylsulfonylmethyl) ether, uricase, peroxidase, a leuco dye in a suitable solvent such as a dispersion of 2(3,5-dimethoxy-4-hydroxyphenyl) 4,5-bis-(4-dimethylamino phenyl) imidazole in 2,4-di-n-pentylphenol, and a borate buffer at pH 9.

The carrier will typically be prepared by coating a solution or dispersion of carrier material, polymer, and reagents on a surface from which the dried film or layer of carrier can then be physically stripped. If the element is multi-layered, multiple coatings can be made directly upon each other as described in U.S. Pat. No. 3,992,158. Particular reagents will be added in the proportions already known in the art. The polymer of choice will usually be incorporated in proportions such that the polymer will comprise from about 20 percent to about 50 percent of the total weight of the carrier material plus the polymer.

As previously described, the elements of the present invention are used by contacting them with the aqueous liquid to be analyzed and calculating the concentration of predetermined analyte in the aqueous liquid from a spectrophotometric measurement of the density of detectable product formed within the element. A variety of different elements can be prepared in accordance with the invention and can be adapted for use in carrying out a wide variety of chemical analyses, not only in the field of clinical chemistry but also in chemical research and in chemical process control applications.

The following examples are provided to further illustrate specific embodiments of the invention and their advantages over analytical elements of the prior art. In these examples "Polymer No. 1" refers to
Poly(methyl acrylate-co-3-acryloyloxypropane≡sulfonic acid, sodium salt-co-2-acetoacetoxyethyl methacrylate) (weight ratio 88.75:4.75:6.5),
and "Polymer No. 2" refers to
Poly(methyl acrylate-co-2-acrylamido-2-methyl≡propanesulfonic acid-co-2-acetoacetoxyethyl methacrylate (weight ratio 88.75:4.75:6.5).

EXAMPLE 1

Improved Reagent Stability In Elements For Glucose Analysis

Several multilayer elements for the analysis of glucose in aqueous liquids were prepared, differing in formulations as indicated:

Element A—Control (contains none of Polymer No. 1)

A polyethylene terephthalate film support was coated with a carrier comprising deionized gelatin (21.5 g/m$^2$), glycerol (2.15 g/m$^2$), glucose oxidase (10,000 U/m$^2$), peroxidase (10,000 U/m$^2$), 7-hydroxy-1-naphthol (0.66 g/m$^2$), 4-amino-antipyrine HCl (0.86 g/m$^2$), and a phosphate buffer system (pH 6.0). A subbing layer and a blushed polymer spreading layer comprising cellulose acetate (6.6 g/m$^2$) and TiO$_2$ (46.0 g/m$^2$) were then applied.

Element B—(Contains Polymer No. 1)

Same as Element A except that in place of glycerol Polymer No. 1 (21.5 g/m$^2$) was added.

Element C—(Contains less gelatin and more Polymer No. 1 than Element B)

Same as Element B except that the amount of deionized gelatin in the carrier was 16 g/m$^2$ and the amount of Polymer No. 1 was 24.2 g/m$^2$.

The elements were stored at room temperature (78° F.) and 50% RH. Density readings at a wavelength of 540 nm were then taken of the background (i.e. dry element) and also of elements spotted with standard solutions containing 800 mg% glucose. Results, shown in Table 1, indicate that the elements containing Polymer No. 1 exhibited significantly less decrease in the density in a dry element (background) and in the density in an element spotted with glucose solution after storage for 16 and 24 weeks than the elements containing none of polymer No. 1. This indicates significantly improved reagent stability in the elements containing Polymer No. 1.

TABLE 1

| Effect Of Polymer No. 1 On Elements For Glucose Assay | | | |
| --- | --- | --- | --- |
| | | % Deterioration (% Change In Density From Fresh Element) | |
| Element | Storage Time (weeks) | Dry Element | Glucose-Spotted Element |
| (control) A | 16 | 46 | 20 |
| B | 16 | 11 | 5 |
| C | 16 | 0 | 4 |
| (control) A | 24 | 70 | 19 |
| B | 24 | 26 | 0 |
| C | 24 | 9 | 2 |

EXAMPLE 2

Comparison Of Two Polymers

Two elements (D and E) were prepared as in Example 1 except that the carrier of element D contained 16.0 g/m$^2$ of deionized gelation and 16.0 g/m$^2$ of Polymer No. 1, and element E contained 16 g/m$^2$ of deionized gelatin and 16.0 g/m$^2$ of Polymer No. 2. Also, the buffer system used in the elements was 3,3-dimethyl glutaric acid (1.96 g/m$^2$) at pH 5.0.

Density readings were taken of the dry background and of elements spotted with a standard solution containing 600 mg% glucose after keeping for 24 weeks at room temperature (78° F. and 50% RH), refrigerated (42°, 50% RH) and frozen (−10° F., 50% RH).

As shown in Table 2, these polymers behaved essentially the same regarding keeping properties and sensitivity to the glucose standard. (Note that the background density readings were made in millivolts, which are inversely proportional to density units.)

TABLE 2

Comparison Of Polymers Nos. 1 and 2

| Element | Temp/% RH | Background mV | $D_R$ Glucose-Spotted Element |
|---|---|---|---|
| D | 78/50 | 727 | 1.406 |
| | 42/50 | 750 | 1.368 |
| | −10/50 | 776 | 1.393 |
| E | 78/50 | 713 | 1.407 |
| | 42/50 | 737 | 1.377 |
| | −10/50 | 776 | 1.341 |

EXAMPLE 3

Improved Keeping In Elements For The Determination Of Uric Acid

Several multilayer elements for the analysis of uric acid in aqueous liquids were prepared according to the following:

A polyethylene terephthalate film support was coated with a carrier comprising deionized gelatin (10.8 g/m$^2$), bis(vinylsulfonylmethyl ether) (0.129 g/m$^2$), peroxidase (6500 U/m$^2$), uricase (215 U/m$^2$), a dispersion of 2(3,5-dimethoxy-4-hydroxyphenyl)-4,5-bis(4-dimethylamino phenyl) imidazole (0.14 g/m$^2$) in 2,4-di-n-amylphenol (1.35 g/m$^2$), and borate buffer at pH 9.

In addition, the carrier layers of Elements G and H contained 5.4 g/m$^2$ and 10.8 g/m$^2$ of Polymer No. 1 respectively. Element F contained no such polymer.

Above the carrier layer was coated a gelatin layer comprising deionized gelatin (5.4 g/m$^2$), and bis (vinyl sulfonyl methyl)ether (0.065 g/m$^2$) in borate buffer at pH 9, a subbing layer comprising poly(n-isopropyl acrylamide) (0.3 g/m$^2$) and a spreading layer comprising TiO$_2$ (46.0 g/m$^2$) and cellulose acetate (6.6 g/m$^2$).

The elements were then evaluated for changes in density of dry background and density after spotting with a 15.0 mg% uric acid solution after incubation for 0, 8, and 24 weeks at 78° F./50% RH.

As can be seen in Table 3, inclusion of Polymer No. 1 in the carrier layer of the uric acid element produces substantially less change in dry background and response over time, thereby increasing the useful life of the element significantly.

Essentially the same results were obtained when Polymer No. 2 was used in the uric acid element instead of Polymer No. 1.

TABLE 3

Effect Of Polymer No. 1 On Elements For Uric Acid Assay

| | | % Deterioration (% Change In Density From Fresh Element) | |
|---|---|---|---|
| Element | Storage Time (weeks) | Dry Element | Uric Acid-Spotted Element |
| (control) F | 8 | 14 | * |
| G | 8 | 7 | * |
| H | 8 | 4 | * |
| (control) F | 24 | 16 | 59 |
| G | 24 | 11 | 32 |
| H | 24 | 8 | 30 |

*Data not available.

EXAMPLE 4

Multilayer analytical elements for the determination of triglycerides in body fluids were prepared as follows:

A polyethylene terephthalate support was coated with a chemistry layer comprising deionized gelatin (5.4 g/m$^2$), dimedone (0.33 g/m$^2$), Triton X-100 (0.39 g/m$^2$), 2-(3,5-dimethoxy-4-hydroxyphenyl)-4,5-bis(4-dimethylaminophenyl) imidazole (0.4 g/m$^2$), in (2,4-di-n-amylphenol (4.0 g/m$^2$), [bis(vinylsulfonylmethyl)]ether (BVSME) (0.03 g/m$^2$), MgCl$_2$ (0.01 g/m$^2$), ATP (1.35 g/m$^2$), peroxidase (6997 U/m$^2$), glycerol kinase (323 U/m$^2$), α-glycerophosphate oxidase (2831 U/m$^2$), Polymer No. 1 (5.38 g/m$^2$) and 0.05 M phosphate buffer, pH 7.0; a gel pad comprising deionized gelatin (5.4 g/m$^2$), Triton X-100 (0.06 g/m$^2$), BVSME (0.03 g/m$^2$), Polymer No. 1 (5.4 g/m$^2$) and 0.05 M phosphate buffer, pH 7.0; an enzyme layer comprising Lipase M (3.24 g/m$^2$), poly[N-isopropylacrylamide-co-2-(methacryloyloxy) ethyltrimethylammonium methosulfate-co-2-hydroxyethyl acrylate] (weight ratio 70:20:10) (1.08 g/m$^2$), and Triton X-100 (0.08 g/m$^2$); a subbing layer comprising poly-n-isopropylacrylamide; and a spreading layer comprising TiO$_2$ (50.0 g/m$^2$), cellulose acetate (7.0 g/m$^2$), Triton X-100 (5.5 g/m$^2$).

A second element was prepared in the same manner, except no Polymer No. 1 was included in either the chemistry layer or gel pad. The freshly prepared elements were each tested with solutions containing 0–300 mg/dl triglyceride. FIG. 1 shows that higher densities are obtained with this dye system when a polymer such as Polymer No. 1 is included.

EXAMPLE 5

Elements, prepared as described in Example 4 above, were incubated for 4 weeks at 78° F. and 50% RH and 8 weeks at 42° F. and 50% RH. The elements were subsequently tested with (1) Cordis, a commercial preparation of triglycerides (∼3.52 mM or 340 mg/dl); (2) glycerol (∼3.52 mM in 7% albumin and 0.155 M NaCl); (3) α-glycerophosphate (7.04 mM in 7% albumin/saline); (4) H$_2$O$_2$ (3.52 mM in water).

Results, shown in FIG. 2 (a, b, c, d) indicate that the addition of Polymer No. 1 greatly improves peroxidase stability in this element. As shown in Curve B, however, glycerol kinase stability is not improved by Polymer No. 1 at 78° F. and 50% RH.

The invention has been described in detail with reference to certain preferred embodiments thereof, but it will be understood that variations and modifications can be effected within the spirit and scope of the invention.

What is claimed is:

1. In an element for the analysis of a predetermined analyte in an aqueous liquid, said element comprising:
   (a) a carrier permeable to said aqueous liquid and to said predetermined analyte and,
   (b) dispersed in said carrier, reagents capable of interacting with or facilitating interaction with said predetermined analyte or its reaction products to yield a detectable product, one of said reagents comprising peroxidase, the improvement comprising having dispersed in said carrier in addition to said reagents a polymer in an amount sufficient to impart stability to said peroxidase, said amount comprising from about 20 percent to about 50 percent of the total weight of said carrier material plus said polymer, said polymer comprising:

1. (1) from about 80 to about 98 percent by weight of recurring units derived from one or more hydrophobic, addition-polymerizable monomers selected from the group consisting of an alkyl acrylate, an alkyl methacrylate, styrene and a substituted styrene, (2) from about 1 to about 20 percent by weight of recurring units derived from one or more anionic monomers selected from the group consisting of an acrylic acid, an acrylic acid salt, a methacrylic acid, a methacrylic acid salt, a sulfonic acid, a sulfonic acid salt, a sulfonate, a sulfate, a phosphate and a phosphorate, and (3) from 0 to about 15 percent by weight of recurring units derived from one or more crosslinkable, active methylene group-containing monomers.

2. An element as described in claim 1 wherein said reagents further comprise an enzyme capable of catalyzing the oxidation of said predetermined analyte to a peroxide and an indicator composition oxidizable by said peroxide in the presence of peroxidase to yield a detectable product.

3. An element as described in claim 1 wherein said reagents further comprise a compound for adjusting pH.

4. An element as described in claim 1 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

5. An element as described in claim 1 which comprises more than one layer, said carrier comprising one of said layers.

6. An element as described in claim 1 wherein said carrier comprises a layer coated on a support material.

7. An element as described in claim 1 wherein a subbing layer is coated on said carrier and a spreading-reflecting layer is coated on the subbing layer.

8. In an element for the analysis of a predetermined analyte in an aqueous liquid, said element comprising:
   (a) a carrier permeable to said aqueous liquid and to said predetermined analyte and
   (b) dispersed in said carrier, reagents capable of interacting with or facilitating interaction with said predetermined analyte or its reaction products to yield a detectable product, one of said reagents comprising peroxidase, the improvement comprising having dispersed in said carrier in addition to said reagents a polymer comprising:
   (1) from about 80 to about 98 percent by weight of recurring units derived from one or more hydrophobic, addition-polymerizable monomers selected from the group consisting of an alkyl acrylate, an alkyl methacrylate, styrene, and a substituted styrene,
   (2) from about 1 to about 20 percent by weight of recurring units derived from one or more anionic monomers selected from the group consisting of an acrylic acid, an acrylic acid salt, a methyacrylic acid, a methyacrylic acid salt, a sulfonic acid, a sulfonic acid salt, a sulfonate, a sulfate, a phosphate, and a phosphorate, and
   (3) from 0 to about 15 percent by weight of recurring units derived from one or more crosslinkable, active methylene group-containing monomers, said polymer comprising from about 20 percent to about 50 percent of the total weight of said carrier plus said polymer.

9. An element as described in claim 8 wherein said reagents further comprise an enzyme capable of catalyzing the oxidation of said predetermined analyte to a peroxide and an indicator composition oxidizable by said peroxide in the presence of peroxidase to yield a detectable product.

10. An element as described in claim 8 wherein said reagents further comprise a compound for adjusting pH.

11. An element as described in claim 8 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

12. An element as described in claim 8 which comprises more than one layer, said carrier comprising one of said layers.

13. An element as described in claim 8 wherein said carrier comprises a layer coated on a support material.

14. An element as described in claim 8 wherein a subbing layer is coated on said carrier and a spreading-reflecting layer is coated on the subbing layer.

15. In an element for the analysis of a predetermined analyte in an aqueous liquid, said element comprising:
   (a) a carrier permeable to said aqueous liquid and to said predetermined analyte and,
   (b) dispersed in said carrier, reagents capable of interacting with or facilitating interaction with said predetermined analyte or its reaction products to yield a detectable product, one of said reagents comprising peroxidase, the improvement comprising having dispersed in said carrier in addition to said reagents a polymer in an amount sufficient to impart stability to said peroxidase, said amount comprising from about 20 percent to about 50 percent of the total weight of said carrier material plus said polymer, said polymer being selected from the group consisting of:

poly(methyl acrylate-co-3-acryloxyloxypropane≡sulfonic acid, sodium salt-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 85:10:5);

poly(n-butyl acrylate-co-3-acryloyloxypropane≡sulfonic acid, sodium salt-co-2-acetoacetoxyethyl methacrylate) (weight ratio 91.25:4.75:4.0); and poly(n-butyl acrylate-co-2-acrylamido-2-methylpropane sulfonic acid-co-2-acetoacetoxyethyl methacrylate) (weight ratio 85:10:5).

16. In an element for the analysis of a predetermined analyte in an aqueous liquid, said element comprising:
   (a) a carrier permeable to said aqueous liquid and to said predetermined analyte and
   (b) dispersed in said carrier, reagents capable of interacting with or facilitating interaction with said predetermined analyte or its reaction products to yield a detectable product, one of said reagents comprising peroxidase, the improvement comprising having dispersed in said carrier in addition to said reagents a polymer selected from the group consisting of Poly(methyl acrylate-co-3-acryloyloxypropane≡sulfonic acid, sodium salt-co-2-acetoacetoxyethyl methacrylate) (weight ratio 88.75:4.75:6.5);

Poly(methyl acrylate-co-2-acrylamido-2-methyl≡propanesulfonic acid-co-2-acetoacetoxyethyl methacrylate) (weight ratio 88.75:4.75:6.5);

Poly(methyl acrylate-co-2-acrylamido-2-methyl≡propanesulfonic acid-co-2-acetoacetoxyethyl methacrylate) (weight ratio=85:10:5);

Poly(n-butyl acrylate-co-3-acryloyloxypropane≡sulfonic acid, sodium salt-co-2-acetoacetoxyethyl methacrylate) (weight ratio 91.25:4.75:4.0); and Poly(n-butyl acrylate-co-2-acrylamido-2-methylpropane sulfonic acid-co-2-acetoacetoxyethyl methacrylate) (weight ratio 85:10:5), said polymer comprising from about 20 percent to about 50 percent of the total weight of said carrier plus said polymer.

17. An element as described in claim 13 wherein said reagents further comprise an enzyme capable of catalyzing the oxidation of said predetermined analyte to a peroxide and an indicator composition oxidizable by said peroxide in the presence of peroxidase to yield a detectable product.

18. An element as described in claim 13 wherein said reagents further comprise a compound for adjusting pH.

19. An element as described in claim 13 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

20. An element as described in claim 13 which comprises more than one layer, said carrier comprising one of said layers.

21. An element as described in claim 13 wherein said carrier comprises a layer coated on a support material.

22. An element as described in claim 13 wherein a subbing layer is coated on said carrier and a spreading-reflecting layer is coated on the subbing layer.

23. In an element for the analysis of glucose in aqueous liquids, said element comprising:
  (a) a carrier permeable to said aqueous liquid and to glucose and,
  (b) dispersed in said carrier, reagents comprising glucose oxidase, peroxidase, 7-hydroxy-1-naphthol, 4-aminoantipyrine HCL and a phosphate buffer system (pH 6), the improvement comprising having dispersed in said carrier in addition to said reagents a polymer in an amount sufficient to impart stability to said peroxidase, said amount comprising from about 20 percent to about 50 percent of the total weight of said carrier material plus said polymer, said polymer being selected from the group consisting of:

poly(methyl acrylate-co-3-acryloxyloxypropane≡sulfonic acid, sodium salt-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 85:10:5);

poly(n-butyl acrylate-co-3-acryloyloxypropane≡sulfonic acid, sodium salt-co-2-acetoacetoxyethyl methacrylate) (weight ratio 91.25:4.75:4.0); and poly(n-butyl acrylate-co-2-acrylamido-2-methylpropane sulfonic acid-co-2-acetoacetoxyethyl methacrylate) (weight ratio 85:10:5).

24. An element as described in claim 23 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

25. An element as described in claim 23 wherein said polymer comprises from about 20 percent to about 50 percent of the total weight of said carrier plus said polymer.

26. An element as described in claim 23 wherein the carrier is a layer comprising deionized gelatin coated on a polyethylene terephthalate film support and said carrier is overcoated with a subbing layer and a blushed-polymer, spreading-reflecting layer comprising cellulose acetate and titanium dioxide.

27. In an element for the analysis of uric acid in aqueous liquids, said element comprising:
  (a) a carrier permeable to said aqueous liquid and to uric acid and,
  (b) dispersed in said carrier, reagents comprising bis(-vinylsulfonylmethyl)ether, uricase, peroxidase, a dispersion of 2-(3,5-dimethoxy-4-hydroxyphenyl)-4,5-bis-(4-dimethylaminophenyl)imidazole in 2,4-di-n-pentylphenol, and a borate buffer (pH 9), the improvement comprising having dispersed in said carrier in addition to said reagents a polymer in an amount sufficient to impart stability to said peroxidase, said amount comprising from about 20 percent to about 50 percent of the total weight of said carrier material plus said polymer, said polymer being selected from the group consisting of:

poly(methyl acrylate-co-3-acryloxyloxypropane≡sulfonic acid, sodium salt-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 88.75:4.75:6.5);

poly(methyl acrylate-co-2-acrylamido-2-methyl≡propanesulfonic acid-co-2-acetoacetoxyethyl methacrylate) (weight ratio 85:10:5);

poly(n-butyl acrylate-co-3-acryloyloxypropane≡sulfonic acid, sodium salt-co-2-acetoacetoxyethyl methacrylate) (weight ratio 91.25:4.75:4.0); and poly(n-butyl acrylate-co-2-acrylamido-2-methylpropane sulfonic acid-co-2-acetoacetoxyethyl methacrylate) (weight ratio 85:10:5).

28. An element as described in claim 27 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

29. An element as described in claim 27 wherein said polymer comprises from about 20 percent to about 50 percent of the total weight of said carrier plus said polymer.

30. An element as described in claim 27 wherein the carrier is a layer comprising deionized gelatin coated on a polyethylene terephthalate film support and said carrier is overcoated with a layer comprising deionized gelatin, bis(vinylsulfonylmethyl) ether, borate buffer (pH9), a subbing layer comprising poly(n-isopropyl acrylamide) and a blushed-polymer, spreading-reflecting layer comprising cellulose acetate and titanium dioxide.

* * * * *